United States Patent [19]

Lu-Chang et al.

[11] Patent Number: 5,683,877
[45] Date of Patent: Nov. 4, 1997

[54] METHOD FOR IDENTIFYING A NUCLEOTIDE BASE PAIR AT A POINT MUTATION SITE IN A DNA TARGET USING A MISMATCH REPAIR ENZYME

[75] Inventors: A-Lien Lu-Chang, Columbia; Ih-Chang Hsu, Ellicott City, both of Md.

[73] Assignee: The University of Maryland at Baltimore, Baltimore, Md.

[21] Appl. No.: 465,798

[22] Filed: Jun. 6, 1995

Related U.S. Application Data

[63] Continuation of Ser. No. 309,629, Sep. 21, 1994, abandoned, which is a continuation of Ser. No. 859,072, Mar. 27, 1992, abandoned.

[51] Int. Cl.$^6$ .................... C12Q 1/68; C12P 19/34
[52] U.S. Cl. .................... 435/6; 435/91.2; 935/77; 935/78
[58] Field of Search .................... 435/6, 91.2, 191, 435/200; 935/77, 78

[56] References Cited

U.S. PATENT DOCUMENTS 5,459,039 10/1995 Modrich et al. .................... 435/6

OTHER PUBLICATIONS

Bos, "Ras Oncogenes in Human Cancer: A Review", *Cancer Research* 49, pp. 4682–4689, (1989).
Change & Lu, "Base Mismatch-Specific Endonuclease Activity in Extracts from *Saccharomyces cerevisiae*", *Nucleic Acids Research* 19, pp. 4761–4766, (1991).
Chehab et al., "Detection of Sickle Cell Anaemia and Thalassaemias", *Nature* 329, pp. 293–294, (1987).
Conner et al., "Detection of Sickel Cell β$^s$–Globin Allele by Hybridization with Synthetic Oligonucleotides", *Proc Natl. Acad. Sci.* 80, pp. 278–282, (1983).
Hennecke, "The Vsr Gene Product of *E. Coli* K–12 is a Strad– and Sequence–Specific DNA Mismatch Endonuclease", *Nature* 353, pp. 776–778, (1991).
Lieb, "Specific Mismatch Correction in Bacteriophage Lambda Crosses by Very Short Patch Repair", *Molecular and General Genetics* 191, pp. 118–125, (1983).
Lu & Chang, "A Novel Nucleotide Excision Repair for the Conversion of an A/G Mismatch to C/G Base Pai in *E. Coli*", *Cell* 54, pp. 805–812, (1988).
Lu & Chang, "Repair of Single Base–Pair Transversion Mismatches of . . . Gene Functions", *Genetics* 118, pp. 593–600, (1988).
Myers et al., "Detection and Localization of Single Base Changes by Denaturing Gradient Gel Electrophoresis", *Methods in Enzymology* 155, pp. 501–527, (1987).
Myers et al., "Detection of Single Base Substitutions by Ribonclease Cleavage at . . . Duplexes", *Science* 230, pp. 1242–1246, (1985).
Saiki et al., "Enzymatic Amplification of β–Globin Genomic Sequences and Restriction Site . . . Anemia", *Science* 230, pp. 1350–1354, (1985).
Tsai-Wu et al., "Nucleotide Sequence of the *Escherichia Coli* MicA Gene Required for A/G–Specific . . . and MutY", *Journal of Bacteriology* 173, pp. 1902–1910, (1991).
Wiebauer & Jiricny, "In Vitro Correction of G·T Mispairs to G·C Pairs in Nuclear . . . Cells", *Nature* 339, pp. 234–236, (1989).
Wiebauer & Jiricny, "Mismatch–Specific Thymine DNA Glycosylase and DNA Polymerase β Mediate the Correction . . . Human Cells", *Proc. Natl. Acad. Sci.* 87, pp. 5842–5845 (1990).
Yeh et al., "Two Nicking Enzyme Systems Specific for Mismatch–Containing DNA in Nuclear Extracts from Human Cells", *The Journal of Biological Chemistry* 266, pp. 6480–6484, (1991).

*Primary Examiner*—Lisa B. Arthur
*Attorney, Agent, or Firm*—Sughrue,Mion,Zinn,Macpeak & Seas, PLLC

[57] ABSTRACT

This invention relates to a method for identifying single base pair mismatches in nucleic acids using mismatch endonucleases and a set of labeled oligonucleotide probes which hybridize to mismatch sequences in the target nucleic acid such that a detectable enzyme-nucleic acid-probe complex forms or labeled cleaved fragments form when a base pair mismatch is present.

11 Claims, No Drawings

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:
        ( A ) LENGTH: 115 base pairs
        ( B ) TYPE: nucleic acid
        ( C ) STRANDEDNESS: single
        ( D ) TOPOLOGY: linear ( i i ) MOLECULE TYPE: synthetic DNA ( i i i ) HYPOTHETICAL: NO ( x i ) SEQUENCE DESCRIPTION: SEQ ID NO:1:

```
AATTGTCCTT AAGCTTTCTT CCCTTCCTTT CTCGCCACGT TCGCCGAATT        50

AGGCTTTCCC CGTCAAGCTC AAATCGGGGG CTCCCTTTAG GGTTCCGATC        100

TCGAGCTTTA CGGCC                                              115
```

( 2 ) INFORMATION FOR SEQ ID NO:2:

( i ) SEQUENCE CHARACTERISTICS:
        ( A ) LENGTH: 110 base pairs
        ( B ) TYPE: nucleic acid
        ( C ) STRANDEDNESS: single
        ( D ) TOPOLOGY: linear ( i i ) MOLECULE TYPE: synthetic DNA ( i i i ) HYPOTHETICAL: NO ( x i ) SEQUENCE DESCRIPTION: SEQ ID NO:2:

```
CCGGGGCCGT AAAGCTCGAG ATCGGAACCC TAAAGGGAGC CCCCGATTTA        50

GAGCTTGACG GGGAAAGCCG AATTCGGCGA ACGTGGCGAG AAAGGAAGGG        100
```

AAGAAAGCTT 110

(2) INFORMATION FOR SEQ ID NO:3:

(i) SEQUENCE CHARACTERISTICS:
        (A) LENGTH: 107 base pairs
        (B) TYPE: nucleic acid
        (C) STRANDEDNESS: single
        (D) TOPOLOGY: linear (ii) MOLECULE TYPE: synthetic DNA (iii) HYPOTHETICAL: NO (xi) SEQUENCE DESCRIPTION: SEQ ID NO:3:

TTGGGGTGAA ACCTGTTTGT TGGACATACT GGATACAGCT GGACGAGAAG 50

AGTACAGTGC CATGAGAGAC CAATACATGA GGACAGGCGA AGGCTTCCTC 100

TGTGTAT 107

(2) INFORMATION FOR SEQ ID NO:4:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ii) MOLECULE TYPE: synthetic DNA (iii) HYPOTHETICAL: NO (xi) SEQUENCE DESCRIPTION: SEQ ID NO:4:

GGTGGACATA CTGGATACAG CTGGACGAGA AGAGTACAGT GCCATGAGAG 50

(2) INFORMATION FOR SEQ ID NO:5:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: synthetic DNA (iii) HYPOTHETICAL: NO (xi) SEQUENCE DESCRIPTION: SEQ ID NO:5:

GGTGAAACCT GTTTGTTGGA 20

(2) INFORMATION FOR SEQ ID NO:6:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: synthetic DNA (iii) HYPOTHETICAL: NO (xi) SEQUENCE DESCRIPTION: SEQ ID NO:6:

ATACACAGAG GAAGCCTTCG 20

(2) INFORMATION FOR SEQ ID NO:7:

(i) SEQUENCE CHARACTERISTICS:
        (A) LENGTH: 20 base pairs
        (B) TYPE: nucleic acid

```
            ( C ) STRANDEDNESS: single
            ( D ) TOPOLOGY: linear ( i i ) MOLECULE TYPE: synthetic DNA ( i i i ) HYPOTHETICAL: NO ( x i ) SEQUENCE DESCRIPTION: SEQ ID NO:7:

TGGACATACT GGATACAGCT                                                   20

( 2 ) INFORMATION FOR SEQ ID NO:8:

( i ) SEQUENCE CHARACTERISTICS:
            ( A ) LENGTH: 20 base pairs
            ( B ) TYPE: nucleic acid
            ( C ) STRANDEDNESS: single
            ( D ) TOPOLOGY: linear ( i i ) MOLECULE TYPE: synthetic DNA ( i i i ) HYPOTHETICAL: NO ( x i ) SEQUENCE DESCRIPTION: SEQ ID NO:8:

CTCTCATGGC ACTGTACTCT                                                   20

( 2 ) INFORMATION FOR SEQ ID NO:9:

( i ) SEQUENCE CHARACTERISTICS:
            ( A ) LENGTH: 30 base pairs
            ( B ) TYPE: nucleic acid
            ( C ) STRANDEDNESS: single
            ( D ) TOPOLOGY: linear ( i i ) MOLECULE TYPE: synthetic DNA ( i i i ) HYPOTHETICAL: NO ( x i ) SEQUENCE DESCRIPTION: SEQ ID NO:9:

GATCGAATTC GATTCTTACA GAAAACAAGT                                        30

( 2 ) INFORMATION FOR SEQ ID NO:10:

( i ) SEQUENCE CHARACTERISTICS:
            ( A ) LENGTH: 30 base pairs
            ( B ) TYPE: nucleic acid
            ( C ) STRANDEDNESS: single
            ( D ) TOPOLOGY: linear ( i i ) MOLECULE TYPE: synthetic DNA ( i i i ) HYPOTHETICAL: NO ( x i ) SEQUENCE DESCRIPTION: SEQ ID NO:10:

CTAGTTCGAA TCCTAGTACC TGTAGAGGTT                                        30
```

METHOD FOR IDENTIFYING A NUCLEOTIDE BASE PAIR AT A POINT MUTATION SITE IN A DNA TARGET USING A MISMATCH REPAIR ENZYME

This is a continuation of application No. 08/309,629 filed 21 Sep. 1994, now abandoned, which is a continuation of application No. 07/859,072 filed 27 Mar. 1992, now abandoned.

Portions of the research described herein were supported in part by the National Institutes of Health, Department of Health and Human Services.

FIELD OF THE INVENTION

The invention relates to a method for detecting gene mutations in nucleic acids. The method can be used to identify an altered base at a specific site.

BACKGROUND OF THE INVENTION

Because many human diseases arise by single base pair changes in genes, the analysis of base pair mismatches and mutation has important implications in biomedical research and in medicine. For example, single base mutations at codons 12, 13 or 61 of one of the three ras genes occur in a significant number of human cancers, the highest incidence being found in adenocarcinomas of the pancreas (90%), the colon (50%) and lung (30%), in thyroid tumors (50%) and in myeloid leukemia (30%). Bos (1989) *Canc. Res.*, 49, 4682–4689. A considerable number of human genetic diseases are known to be caused by point mutation (see for example the latest edition of "Mendelian Inheritance in Man" by V. A. McKusick).

Single base changes can be neutral, that is, encode the same amino acid if occurring in an exon, occurring at a non-critical site in an intron or may result in a conservative amino acid substitution; can result in an amino acid change that yields a less fit, albeit functional, gene product; or can result in a deleterious allele which could affect the survival of the host organism.

Single base substitutions that yield effectively neutral changes contribute to normal population heterogeneity, also known as polymorphism or balanced polymorphism. The most prevalent allele or the allele believed to be the oldest in a population is identified as the wild type allele. Those single base substitutions that reduce the fitness of the organism are commonly known as mutations. For those mutations that reduce fitness, predispose an organism to a disease state or that have reduced penetrance or delayed expression, it would be beneficial to have the capability of diagnosing or identifying the allele carried by the target organism.

Direct gene analysis, particularly for the detection of single base mutation, can be obtained by a variety of techniques. For example, restriction fragment length polymorphism results from alterations in the recognition sequence of a restriction endonuclease. The discovery of a restriction fragment length polymorphism enabled the diagnosis of sickle cell anemia which arises from a single amino acid change in β globin. But the recognition site of restriction endonucleases generally is from 4–10 base pairs, there are large numbers of restriction endonucleases specific for unique recognition sites and the recognition sites, if organized randomly in the genome, would be distributed at a frequency that correlates with the number of base pairs in the restriction site. Thus, only a small portion of the genome is monitored by any one enzyme.

Another means for identifying base substitution is direct sequencing of a nucleic acid fragment. The two prevalent methods are the Maxam/Gilbert method (Maxam & Gilbert (1980) *Meth. Enz.*, 65, 499–560) and the dideoxy method (Sanger et al. (1977) *Proc. Natl. Acad. Sci.*, 74, 5463–5467). Although the use of the polymerase chain reaction (PCR) (Saiki et al. (1985) *Science*, 230, 1350–1353) can facilitate sequencing, direct gene sequencing remains a labor intensive and tedious means.

Because mismatches often cause anomalous mobility of nucleic acid fragments in electrophoretic procedures, methods have been devised for distinguishing mismatched duplexes from matched duplexes, see for example Myers et al. (*Meth. Enz.* (1987) 155, 501–527). Mismatches can be obtained by hybridizing sequences from wild type and mutant genes or from a sample with a synthesized oligonucleotide. The sensitivity of detecting mismatched duplexes can be enhanced by conducting the electrophoretic separation under denaturing conditions, Myers et al., supra.

Another method for detecting mismatches is using RNase A (Myers et al. (1985) *Science*, 230, 1242–1246). For example, a specific probe is hybridized to target RNA or DNA and then exposed to RNase A, which is able to detect mismatches in a duplex structure. The enzyme cleaves at the site of a mismatch. Upon electrophoresis under denaturing conditions, the mismatch is detectable by the presence of nucleic acid fragments which are smaller than the full length duplex. While the RNase A method is not as definitive or as sensitive as sequencing, it is more rapid than sequencing.

Another approach relies on the instability of duplexes comprising an oligonucleotide, see for example Conner et al. (*Proc. Natl. Acad. Sci.* (1983) 80, 278–282). Such duplexes are stable only under well defined hybridization conditions, generally involving salt concentration of the hybridization solution and temperature. Thus, an oligonucleotide which is complementary except for a single mismatch may not remain hybridized to a target sequence if the hybridization conditions are not optimized. That rationale enables the detection of mismatches by hybridizing an oligonucleotide to a target sequence and determining whether a stable duplex molecule results.

A newer method relies on DNA ligase which covalently joins two adjacent oligonucleotides which are hybridized on a complementary target nucleic acid, see for example Landegren et al. (*Science* (1988) 241, 1077–1080). The mismatch must occur at the site of ligation. As with other methods that rely on oligonucleotides, salt concentration and temperature at hybridization are crucial. Another consideration is the amount of enzyme added relative to the DNA concentration.

Another method relies on polymerase chain reaction amplification of specific oligonucleotide primers, see for example Chehab et al. (1987) *Nature*, 329, 293–294). The method offers the advantages of not requiring a large amount of DNA, as is required for restriction fragment length polymorphism analysis, and is more rapid, than for example, the use of allele-specific oligonucleotide hybridization. Furthermore, the method does not require the use of radioactive labels. Wu et al. (1989) *Proc. Natl. Acad. Sci.*, 86, 2757–2760.

Each of the known prior art methods for detecting single base pair mismatches has shortcomings. Hybridization and RNase assays occasionally give false positive or false negative results due to high background or poor enzyme specificity. Methods relying on the use of oligonucleotides require carefully controlled hybridization conditions. The use of allele-specific oligonucleotides also requires finely tuned conditions as one of the pair of PCR primers must be perfectly matched and the other, because of one or more mismatches, must not hybridize for discrimination to be possible. Methods that rely on PCR can have contamination problems and some mismatches can form base pairs thereby producing false results. DNA sequencing cannot detect a base change in a DNA sample which is contaminated with more than 80% of normal DNA.

Denaturing gradient gel or the RNase A methods can assess long stretches of DNA for mismatches, however, those methods are not as sensitive as the ligase method because they are estimated to test only about half of all mutations that involve single nucleotides. Furthermore, less than half of all point mutations give rise to gain or loss of a restriction enzyme cleavage site. Landegren et al. (1988) *Science*, 241, 1077–1080.

All of the methods mentioned above cannot reliably detect a base change in a nucleic acid which is contaminated with more than 80% of a background nucleic acid, such as normal or wild type sequences. Contamination problems are significant in cancer detection wherein a malignant cell, in circulation for example, is present in extremely low amounts. Thus, the methods now in use lack adequate sensitivity to find practical use in a clinical setting. It is desirable for an assay to have a sensitivity of less than 20%, that is, capable of detecting a variant sequence that comprises less than 20% of a sample, and preferably less than 10%.

Accordingly, there is a need for a sensitive and accurate assay for detecting single base pair mismatches which does not require the use of toxic labels, does not require a large amount of a sample, is not labor intensive and is robust. It is particularly advantageous if the assay has a sensitivity of detecting a single base change in a DNA sample contaminated by up to, if not more than, about 99% normal DNA.

There are a class of enzymes that repair mismatches in nucleic acids, and particularly in DNA. Suitable enzymes, for example, are those which specifically cleave nucleic acid strands near mismatches. Some of those enzymes have nucleic acid glycosylase activity as well as apurinic or apyrimidinic endonuclease activity.

For example, a dam methylation-independent pathway in *E. coli* acts unidirectionally on G/T mismatches to restore the G/C pair at the second position within the sequence 5'-CC(A/T)GG. Lieb (1985) *Mol. Gen. Genet.*, 101, 118–125. The enzyme involved with that repair function has been expressed as a fusion protein. Hennecke et al. (1991) *Nature*, 353, 116–118.

Wiebauer & Jiricny (*Nature* (1989) 339, 234–236; *Proc. Natl. Acad. Sci.* (1990) 87, 3842–3845) reported an enzyme obtained from HeLa nuclear extracts capable of correcting G/T mismatches almost exclusively to G/C pairs.

A dam-independent repair pathway specific for A/G mismatches requires expression of the *E. coli* mutY gene product. Lu & Chang (1988) *Genet.*, 108, 593–600; Tsai-Wu et al. (1991) *J. Bacteriol.*, 173, 1902–1910. The repair mechanism is unidirectional resulting in an A to C conversion. The enzyme responsible for the repair activity both binds specifically to A/G mismatches and cleaves the nucleic acid at either side of the adenine residue. There are no incisions on the other strand. The repair system is proposed to convert A/G mismatches to a C/G base pair. Lu & Chang (1988) *Cell*, 54, 805–812.

Similar enzymes specific for A/G mismatches have been found in human (Yang et al. (1991) *J. Biol. Chem.*, 266, 6480–6484) and calf thymus cells. The all-type endonuclease described hereinbelow and obtained from HeLa, calf thymus and yeast cells nicks at eight different base pair mismatches.

SUMMARY OF THE INVENTION

It is an object of the instant invention to provide a sensitive and accurate method for detecting base pair mismatches in nucleic acid sequences and particularly in DNA sequences, such as genomic DNA sequences.

Another object of the instant invention is to provide a method for identifying the nucleotide at a specific site in a nucleic acid without using sequencing methods.

Those and other objects were attained through the development of a method for identifying a nucleotide base at a single site in a nucleic acid comprising:

(a) obtaining single stranded target nucleic acid sequences;

(b) hybridizing oligonucleotides comprising said site to said single stranded nucleic acid sequences, wherein said oligonucleotides may or may not be complementary at said site in said single stranded nucleic acid sequences, to form oligonucleotide-target nucleic acid sequence hybrids;

(c) exposing said nucleic acid sequence hybrids to an enzyme that binds to mismatch bases to form enzyme-nucleic acid complexes or that cleaves one strand containing a mismatched base pair to produce cleaved fragments;

(d) determining the presence of said enzyme-nucleic acid complexes or said cleaved fragments; and e) identifying the nucleotide base at said site by virtue of whether a reaction with an oligonucleotide forms a complex or produces cleaved fragments.

The method is further exemplified wherein said oligonucleotides comprise a first and a second oligonucleotide complementary to a first single stranded nucleic acid and a third and a fourth oligonucleotide complementary to the second single stranded nucleic acid; and wherein said first and said third oligonucleotides comprise A, T, G or C at said site, and said second and said fourth oligonucleotides comprise at said site a base other than that base which hybridizes under normal conditions with the base at said site in said first and said third oligonucleotides.

The instant invention also provides a method for identifying a base pair mismatch at a site in a nucleic acid comprising:

(a) obtaining single stranded target nucleic acid sequences;

(b) hybridizing nucleic acid fragments obtained from wild type cells or oligonucleotides comprising said site to said single stranded nucleic acid sequences, wherein said fragments or said oligonucleotides may or may not be complementary at said site in said single stranded sequence, to form fragment-target nucleic acid hybrids or oligonucleotide-target nucleic acid hybrids;

(c) exposing said nucleic acid hybrids to an enzyme that binds specifically to base pair mismatches to form enzyme-nucleic acid complexes or that cleaves a nucleic acid strand to produce cleaved fragments; and (d) determining the presence of said complexes or said cleaved fragments.

The instant invention also provides a method for detecting the loss of a wild type allele comprising identifying a mismatch between a first nucleic acid obtained from target cells and a second nucleic acid, wherein said first and said second nucleic acids are hybridized to form a duplex and said duplex is exposed to an enzyme which binds to a mismatch base pair to form a complex or which cleaves said first or second nucleic acid to form cleaved fragments and determining the presence of said complex or said cleaved fragments. The second nucleic acid can be obtained from a wild type cell or synthesized.

The instant methods can be useful in the detection of genetic disease, cancer and genetic variability such as normal polymorphisms.

Determining whether cleavage occurred can be accomplished in a variety of art-recognized methods. Thus, such a determination can be accomplished by direct analysis of the sequences, such as by nucleotide sequencing, or by determining fragment lengths following labelling of the nucleic acid sequence, with, for example, radioactive labels, such as $^{32}P$. The use of denaturing gels can facilitate discrimination of the reaction products.

Alternatively, cleavage can be inferred for example, by labelling the nucleic acid sequence at two sites on either side of the target site. Thus, for example, the doubly labelled nucleic acid is fixed to a solid support at one end and following the enzymatic reaction with the mismatch enzyme and a wash, presence of both labels or one label, that on the end fixed to the solid support or that washed away, is assessed. The labels can be the same or different. Preferably the reporter molecules are non-radioactive labels, such as enzymes or dyes.

Detection of mismatches can occur also by determining the presence of enzyme-nucleic acid complexes, for example, by analysis on a native gel, gel retardation assay, essentially as described in Fried & Crothers (*Nucl. Acids Res.* (1981) 9, 6505–6526).

DETAILED DESCRIPTION OF THE INVENTION

The instant invention relates to the use of a class of enzymes capable of mismatch detection and/or repair to detect single base pair mutations in nucleic acids and particularly in DNA, such as in genomic DNA. Any of the class of enzymes capable of identifying or binding to a site of a base pair mismatch and/or cleaving at or about that site can be used in the instant invention.

The instant invention finds utility in the diagnosis of genetic disorders that arise from point mutations. Many cancers, for example, can be traced to point mutations in kinases, growth factors, receptors binding proteins and nuclear proteins. Some of the disorders include cystic fibrosis, xeroderma pigmentosum, ataxia telangiectasia, Bloom's syndrome, the hemoglobinopathies, such as thalassemia and sickle cell disease, other diseases that arise from inborn errors of metabolism, such as phenylketonuria, muscular dystrophy, mental retardation syndromes, such as the fragile X syndrome, Albright's osteodystrophy, specific genes associated with cancer, such as DCC, NF-1, RB, p53, erbA and the Wilm's tumor gene, and various oncogenes, such as abl, erbB, src, sis, ras, fos, myb and myc.

The instant assay can be used on the nucleic acids of a variety of cells, for example, blood cells, amniocytes, that is cells found in the amniotic fluid, bone marrow cells, cells obtained from a biopsy specimen and the like. The nucleic acids can be ribo or deoxyribo nucleic acids. Double stranded nucleic acids are rendered single stranded using known techniques.

The term, "base pair mismatch", indicates a base pair combination that generally does not form in nucleic acids under normal circumstances. For example, when dealing with the bases commonly found in DNA, namely adenine, guanine, cytosine and thymidine, base pair mismatches are those base combinations not including the A-T and G-C pairs normally formed in DNA's.

As used herein, "complementary" indicates normal base pairing between two nucleic acid strands but may include a mismatch at a site.

As used herein, "oligonucleotide" indicates any short segment of nucleic acid which can be obtained as a fragment from a cell, for example as a restriction fragment, or is synthesized in vitro.

An enzyme of the class of enzymes which is suitable in the practice of the instant invention is that described in Lu & Chang (Cell (1988) 54, 805–812) which recognizes the A/G mismatch. The enzyme is obtained from *E. coli* and is identified as MutY (or MicA).

A suitable method for obtaining an enzyme useful in the instant invention is exemplified in a method for obtaining the A/G mismatch enzyme. The A/G mismatch enzyme can be obtained from *E. coli*, such as any wild type strain available from the American Type Culture Collection. The cells are lysed in a suitable buffer such as a buffer comprising about 15 mM Tris-HCl, pH 7.6, about 0.1 mM EDTA, about 0.5 mM DTT and about 0.1 mM PMSF (Buffer A). The cells are lysed by commonly known methods such as freeze-thaw or sonication. The lysate is clarified by centrifugation and the supernatant is treated with about 25% (w/v) streptomycin sulfate. Any insoluble material is removed and solid ammonium sulfate is added to the supernatant to a concentration of about 35%. The precipitate obtained therefrom is suspended in buffer A recited above.

The suspension is dialyzed against the above-noted buffer A. The resulting dialysate is suspended in a suitable buffer such as one comprising about 20 mM potassium phosphate, pH 7.4, about 0.5 mM DTT, about 0.1 mM EDTA and about 0.1 mM PMSF, containing about 0.05 mM potassium chloride (Buffer B).

The resulting solution is passed over a phosphocellulose column and the column is eluted with a linear gradient of about 0.05–0.5M potassium chloride in the above-noted buffer B. Those fractions containing A/G mismatch binding and/or nicking activity, which elute at about 0.3M potassium chloride, are pooled and are applied to a hydroxyapatite column equilibrated with the same buffer B as noted above except that the potassium phosphate concentration is 10 mM and the solution contains 0.01M potassium chloride. The column is eluted with a linear gradient of potassium phosphate (pH 7.4, about 0.01–0.6M) containing 0.5 mM DTT and 0.1 mM PMSF. Active fractions obtained from the column can be stored at −70° C.

Alternatively, the eluate further is dialyzed against a buffer comprising about 20 mM $KPO_4$[pH 7.4], about 0.1 mM EDTA, about 0.5 mM DTT, about 0.5M KCl, about 0.1 mM PMSF and about 10% (v/v) glycerol (Buffer C). The dialysate is applied to a heparin-agarose column and eluted with a 0.1–0.6M KCl gradient in the same buffer C. A/G nicking activity elutes at about 0.38M KCl and the fractions are dialyzed against buffer C. The resulting endonuclease preparation is purified about 1,500 fold.

The gene product of the mutY (or micA) locus of *E. coli* is essential to obtain methylation-independent repair of A/G mismatches. The DNA sequence of the mutY locus has been cloned and found to encode a protein of about 39 kd molecular weight which carries A/G mismatch-specific nicking activity. Tsai-Wu et al. (1991) *J. Bacteriol.*, 173, 1902–1910. The recombinant enzyme can be used in the practice of the instant invention.

The determination of whether an enzyme with the requisite characteristics is obtained can rely either on the capability of a protein to bind specifically to an A/G mismatch or on the capability to cleave at or about an A/G mismatch.

By way of example, the hybrid of phages fl R229 and M28 has an A/G mismatch at position 5621. Boeke (1981) *Mol. Gen. Genet.*, 181, 288–291; Lu et al. (1983) *Proc. Natl. Acad. Sci.*, 80, 4639–4643. Thus, a nucleic acid fragment containing position 5621 can be used in a protein-nucleic acid binding or nicking assay. Alternatively, two annealed oligonucleotides, made in a commercially available DNA synthesizer, which are complementary except at one defined position where an A/G mismatch is configured, can be used as a heteroduplex carrying an A/G mismatch in the above noted assays.

In a binding assay, protein samples are incubated with labelled nucieic acid fragment containing, according to the example above, the A/G mismatch along with non-labeled, non-specific DNA (see Fried & Crothers, supra; Carthew et al., (1985) *Cell*, 43, 439–448). Briefly, protein samples are incubated with labeled target nucleic acid in a buffer comprising about 20 mM Tris-HCl (pH 7.6), about 80 mM NaCl, about 1 mM EDTA and about 2.9% glycerol for about 30 minutes at about 30°. Following incubation, the samples are applied to a polyacrylamide gel (about 4%) using low ionic strength buffers (about 7 mM Tris-HCl, pH 7.5, about 3 mM sodium acetate and about 1 mM EDTA). Protein-nucleic acid complexes migrate slower than nucleic acid fragments alone.

Nicking activity can be determined in a similar fashion as for determining the protein-nucleic acid complexes. Following the incubation period, the nucleic acid samples are denatured, for example, by heat treatment, exposure to formamide or both, and then the samples are applied to a standard denaturing polyacrylamide gel, for example about 8% with about 8M urea, for resolution. Successful nicking is revealed by the presence of one or more smaller-sized nucleic acid fragments as compared to the intact nucleic acid fragment.

A T/G-specific endonuclease can be detected and obtained using the same procedures except using an T/G mismatch-containing nucleic acid.

By configuring other specific combinations of mismatches in the nucleic acid substrate, other enzymes contemplated to be useful in the practice of the instant invention can be identified and purified, such as the "all type" enzyme from HeLa cells, calf thymus and yeast cells described further hereinbelow. Chang & Lu (1991) *Nucl. Acids Res.*, 19, 4761–4766; Yang et al. (1991) *J. Biol. Chem.*, 266, 6480–6484.

The human and yeast all type endonuclease can nick at all eight base pair mismatches. Thus, that enzyme can be used for general screening for any mutations. In that case, polymerase chain reaction (PCR) products from normal and suspected mutant nucleic acids can be hybridized and tested with the all type enzyme. Because different mismatches may be identified with differing efficiencies and sequence environment may have an effect on cleavage, labeling of different ends of the target nucleic acids or PCR products can be used.

It has been found that in the case of the A/G mismatch enzyme of Lu & Chang, supra, the enzyme is active on not only nucleic acids of the endogenous host, *E. coli*, but is active on the nucleic acids of other species as well. Essentially, any nucleic acid containing an A/G mismatch is a suitable substrate for the A/G mismatch enzyme. Thus, in the case of the A/G mismatch enzyme, the enzyme can be used to detect A/G mismatches in agriculturally beneficial species and in humans, for example. That discovery enables the diagnosis of single base pair mismatches or mutation that can give rise to deleterious alleles and disease states. Species specificity does not appear to be a characteristic of the mismatch repair enzymes, similar to the many restriction endonucleases which essentially act on DNA of any species.

Accordingly, in one embodiment, the instant invention relates to a method of detecting specific nucleic acid mutations with a mismatch enzyme, such as the A/G mismatch enzyme, that can be used to determine the presence of specific alleles or aberrant alleles in a nucleic acid, such as the genomic DNA, of an animal or a patient. Uses include prenatal diagnosis of genetic disease or the identification of latent genetic disease, that is diseases with low penetrance or delayed expression. The assays can be practiced essentially aS described above, that is, cells of a patient suspected of carrying a genetic disorder can be obtained, possibly circulating cells such as lymphocytes or by biopsy of a diseased organ, the nucleic acids from the cells are obtained, a specific region optionally can be amplified by PCR, hybridized with normal or wild type nucleic acid or with a specific probe, if necessary, treated with an appropriate restriction endonuclease to provide a fragment containing the suspected base pair mismatch or mutation, exposed to a mismatch enzyme and either the binding assay or the nicking assay is conducted.

In the binding assay and nicking assay described hereinabove, the presence of the protein-nucleic acid complex or of the cleaved fragments can be determined in a number of art-recognized methods, see for example Fried & Crothers (*Nucl Acids Res.* (1981) 9, 6505–6525). For example, the nucleic acid in the binding assay can be tagged with a radioactive label, such as a radiolabelled base (in the nicking assay, either the probe or the target genomic nucleic acid can be labelled to determine if cleavage occurs) and the respective molecular weights and migration distances are inferred therefrom following a separation and/or a sizing procedure, such as electrophoresis. Examples of radioisotopes that can be used include $^3H$, $^{32}P$, $^{35}S$ and $^{125}I$.

In a clinical setting and for general use in many clinical testing laboratories, it is preferable that methods that do not require the use of radiolabelled nucleotides be used. Thus, the nucleic acids can be labelled with biotinylated bases and the presence of the biotin moiety can be determined by the use of avidin or streptavidin labelled reporter molecules, which in turn can be ascertained by the use of the appropriate colorimetric or chemiluminescent substrate. (For example, BRL, Gaithersburg, MD, distributes biotinylated dATP, streptavidin-alkaline phosphatase conjugate and the appropriate phosphatase substrates. Lumigen®-PPG is a suitable substrate distributed by Millipore, Me.)

Similarly, it also is possible to use bases which are labelled with compounds that are luminescent, for example, some automatic nucleic acid sequenators rely on the use of the four common bases each labelled with a compound having a unique color signature. Luminescence is determinable in a liquid scintillation counter, luminometer or by the use of light-sensitive films. Typical examples of luminescent compounds which can be used include fluorescent compounds, such as fluorescein isothiocyanate (Sigma), that emit light upon excitation and chemiluminescent compounds that emit light as a result of a chemical reaction, such as the use of reporter molecules comprising dioxetane derivatives (PhotoGene®, BRL, MD).

In another embodiment, particularly when using the nicking assay, the nucleic acid to be labelled, either the probe or the genomic target sequence, is labeled at both ends, that is on either side of the mismatch. The label may be the same or different. For example, one end may be labelled with biotin and the other end may be labelled with a luminescent compound.

Thus, an intact molecule comprises both labels whereas a cleaved molecule yields two subfragments, each with one label. For example, using fluorescent molecules that emit at different wavelengths or dyes of different color, a nucleic acid can be so labelled and the determination of whether cleavage has occurred is assessed by the presence of both labels in the sample or of only one label, for example, after a washing procedure wherein one end of the doubly labelled nucleic acid is affixed to a solid phase enabling the cleaved fragment carrying the second labelled end to be removed by a washing procedure. If identical labels are used, then the determination is whether a "single dose" or a "double dose" of label is present following the washing procedure.

According to the assay system using the N-ras gene, the sensitivity of the instant assay is at least on the order of 1%, that is the assay can detect tumor cells that are present in a 99% background of normal cells. Thus, the instant assay can identify a sequence variant found at a frequency of one variant out of a hundred.

Accordingly, it is not necessary to obtain a specific biopsy section or to purify a cell population prior to use of the instant assay, such as by flow cytometry. The instant assay enables the detection of a genetic disorder using circulating cells found in a routine specimen.

In another embodiment, the invention contemplates the use of enzymes that recognize specific base pair mismatches for determining the identify of a particular base at a mismatch site whether the mismatched base pair is one of the pairs that is recognized by the enzyme or not.

Four possible oligonucleotide probes are synthesized to span the site of interest. Two of the probes correspond to coding sequences of the gene of interest and another two probes are complementary to the aforementioned two probes. The strategy is outlined in Table 1 wherein probes I and II represent the coding sequence probes and probes III and IV represent the probes complementary to probes I and II, respectively.

TABLE 1

Expected mismatch formation and cleavage results using E. coli A/G endonuclease

| Sequence at the mutation site | I[a] (coding, A) | II[b] (coding, G) | III[a] (noncoding, A) | IV[b] (noncoding, G) |
|---|---|---|---|---|
| A | A* | G | A | A* |
| T | T(−) | T*(−) | A*(−) | G(++)[c] |
| C | A* | G | C | C* |
| G | G(++) | G*(−) | A*(+) | G(−) |
| G | A* | G | G | G* |
| C | C(+) | C*(−) | A*(++) | G(−) |
| T | A* | G | T | T* |
| A | A(−) | A*(++) | A*(−) | G(−) |

*represents the labelled strand
[a]use 5' end-labelled oligonucleotide probe
[b]use unlabelled oligonucleotide to hybridize with labelled PCR amplified target sequence
[c]double positive result indicates A/G mismatch-containing nucleic can be nicked by the endonuclease and shows a lower molecular weight band(s) in the autoradiogram of a sequencing gel; A/C mismatch nicked weakly by the A/G mismatch enzyme In the example of Table 1, probes I and III contain adenine at the position where the mutation occurs whereas probes II and IV contain guanine at that site. The probes containing adenine, probes I and III of Table 1, are end-labelled at the 5' end, for example, with kinase using standard procedures. Probes containing guanine are not labelled. In the hybridization reactions wherein the guanine-containing oligos are used (probes II and IV), the target nucleic acid fragment is labelled.

The target nucleic acid sequence is rendered single stranded and exposed to the various probes in individual reaction vessels to enable duplex formation. Depending on the sequence of the target nucleic acid at the target site, the various probes will generate either no mismatch or a certain base mismatch after hybridization. The resulting duplexes are digested with a specific mismatch enzyme, such as the A/G mismatch enzyme, the T/G mismatch enzyme (Wiebauer & Jiricny (1989) Nature, 339, 234–236), the all-type enzyme (Yeh et al. (1991) J. Biol. Chem., 261, 6480–6484) or combinations of several different enzymes, and the nucleic acid fragments following incubation are identified by denaturing gel electrophoresis.

Any nucleic acid with a specific mismatch, in the cases noted above, an A/G mismatch or a T/G mismatch, can be detected and localized by the presence of one or more subfragments. Thus, in the Example of Table 1, using the A/G mismatch enzyme, if a lower molecular weight fragment noted in the reaction with the target sequence contains an adenine at the site of interest, Table 1, line 1, a digestion product, that is a subfragment, will be observed when the target gene is hybridized with oligonucleotide IV. If the target site is a C (Table 1, line 2), a subfragment will be found in the duplex in which oligonucleotide I is used.

It is not essential that all four reactions be run concurrently to identify the base at the target site. The individual reactions can be run sequentially, or in any combination or order, as identification of the variant base could occur in the first reaction based on the unique pattern of reactivity for each oligonucleotide.

In another embodiment, the invention contemplates the use of a general mismatch enzyme that is not restricted to a specific mismatch, that is, the enzyme is not restricted to recognizing only the A/G mismatch, for example. Such an enzyme has been obtained from bovine, yeast and human and the enzyme can nick at all eight base pair mismatches. Yeh et al. (1991) J. Biol. Chem., 266, 6480–6484. Thus, the general (all type) mismatch enzyme can be used to compare suspected mutant nucleic acid with wild type nucleic acid or in a first screening for any mutation because the site and base at that site may not be known and only a single oligonucleotide probe or the mutant and normal nucleic acids, relative to the target site, need be used. In using the general mismatch enzyme, the artisan must consider that different mismatches may be recognized with different efficiencies and that neighboring sequence environment could have some effect on binding and cleavage. Nevertheless, the general mismatch endonuclease retains the property of cleaving only one of the strands.

To overcome strand specificity that could hinder the detection of a base pair mismatch, other mismatch enzymes, topoisomerases, glycolases and endonucleases, or combinations thereof, can be included in the screening of nucleic acid mismatches. Grilly et al. (1990) Mutat. Res. 236, 253–267.

An example of a general mismatch endonuclease is one obtainable from calf thymus nuclear extracts by a modified method as described in Dignam et al., Nucl. Acids Res., 17, 2437–2448, 1989). Briefly, frozen calf thymus (about 500 g)

is thawed under running cold water, sliced and cleaned of connective tissue and vessels. The tissue slices are placed in solution A comprising about 0.2M sucrose, about 3 mM MgCl$_2$, about 40 mM NaCl, about 0.05 mM PMSF and about 5 mM HEPES, pH 7.9 and homogenized. The homogenate is filtered sequentially through one, two and four layers of cheesecloth prewashed with chilled solution A.

The filtrate is centrifuged at 750×g for seven minutes and the nuclear pellet is washed with solution A. About 250 ml of packed nuclei were suspended in about 500 ml of Solution E comprising about 10% sucrose, about 0.01% NP-40, about 1 mM DTT, about 0.1 mM PMSF, about 0.35M KCl and about 25mM HEPES, pH 7.9 and incubated at about 4° C. for about two hours. The nuclear debris was removed by centrifugation. The supernatant was diluted to 100 mM KCl by adding about two volumes of Buffer A comprising about 20 mM KPO$_4$, pH 7.4, about 0.1 mM EDTA, about 0.5 mM DTT and about 0.1 mM PMSF.

In the case of obtaining an all-type mismatch enzyme from human cells, such as HeLa cells, again a modification of the method of Dignam et al., supra, is employed. The isolated nuclear extract (fraction I) in about 60 ml buffer (comprising about 20 mM HEPES, pH 7.4, about 25% glycerol, about 0.42M NaCl, about 1.5mM MgCl$_2$, about 0.2 mM EDTA, about 0.5 mM PMSF and about 0.5 mM DTT) was mixed with about 440 ml of buffer A (about 20 mM KPO$_4$, pH 7.4, about 0.5 mM DTT, about 0.1 mM EDTA and about 0.1 mMPMSF) containing about 0.05M KCl and the entire mixture is applied to an ion exchange column such as a 140 ml Bio-Rex 70 column (BioRad) equilibrated with buffer A containing about 0.05 mM KCl. Following a wash with the equilibration buffer, the column can be eluted with a linear gradient of KCl (about 0.1–1.0M) in buffer A. The fractions containing the general mismatch endonuclease, which eluted at about 0.8M KCl, are pooled (Fraction II).

Fraction II can be applied to a hydroxyapatite column equilibrated with buffer A containing about 0.05M KCl. After washing with equilibration buffer, the column is eluted with a linear gradient of potassium phosphate (pH 7.4, about 0.01–0.6M) containing about 0.5 M DTT and about 0.1M PMSF. Active fractions, which elute at about 0.4M phosphate buffer, are pooled (fraction III) and dialyzed against buffer A.

The sample can be loaded onto a heparin agarose column and eluted with, for example about 0.7 mM NaCl in buffer A. The eluted sample can be frozen in small aliquots and stored at −70° C.

Presence of the general mismatch endonuclease in the fractions can be determined essentially as described above for the A/G-specific endonuclease using the nucleic acid binding assay or the nicking assay with the appropriate nucleic acid fragments containing a mismatch.

The invention now will be described further by way of the following non-limiting examples. Unless otherwise indicated all amounts are either as (w/w) or (w/v).

EXAMPLE 1

Oligonucleotide primers and repair probes were synthesized using standard phosphoramidite chemistry on an Applied Biosystems DNA synthesizer according to the manufacturer's recommendations. See for example, Beaucage & Caruthers (1981) *Tetra. Lett.*, 22, 1859–1862; Mattencci & Caruthers (1981) *J. Amer. Chem. Soc.*, 103, 3185–3191. The oligonucleotides were purified in 8–25% sequencing gels prior to use. The oligonucleotide denoted as Chang A16 (SEQ ID NO:1) was annealed with oligonucleotide Chang G16 (SEQ ID NO:2) to form duplex DNA with an A/G mismatch at position 51 for use in the endonuclease assay.

TABLE 2

| Sequences of oligonucleotides[1] | |
|---|---|
| Chang A16 | 5'AATTGTCCTTAAGCTTTCTTCCCTTCCTTTCTCGCC ACGTTCGCCGAATTAGGCTTTCCCCGTCAAGCTCAA ATCGGGGGCTCCCTTTAGGGTTCCGATCTCGAGCTTT ACGGCC 3' (SEQ ID NO:1) |
| Chang G16 | 5'CCGGGGCCGTAAAGCTCGAGATCGGAACCCTAAAGG GAGCCCCCGATTTAGAGCTTGACGGGGAAAGCCGAAT TCGGCGAACGTGGCGAGAAAGGAAGGGAAGAAAGCTT (SEQ ID NO:2) |
| Chang 23 107N N-ras-61 probe | 5'TTGGGGTGAAACCTGTTTGTTGGACATACTGGATAC AGCTGGACGAGAAGAGTACAGTGCCATGAGAGACCAA TACATGAGGACAGGCGAAGGCTTCCTCTGTGTAT 3' (SEQ ID NO:3) |
| Chang 31 | 5'GGTGGACATACTGGATACAGCTGGACGAGAAGAGTA CAGTGCCATGAGAG 3' (SEQ ID NO:4) |
| P1 103 bp left primer | 5'GGTGAAACCTGTTTGTTGGA 3' (SEQ ID NO:5) |
| P2 103 bp right primer | 5'ATACACAGAGGAAGCCTTCG 3' (SEQ ID NO:6) |
| P3 48 bp left primer | 5'TGGACATACTGGATACAGCT 3' (SEQ ID NO:7) |
| P4 48 bp right primer | 5'CTCTCATGGCACTGTACTCT 3' (SEQ ID NO:8) |
| P5 210 bp left primer | 5'GATCGAATTCGATTCTTACAGAAAACAAGT 3' (SEQ ID NO:9) |
| P6 210 bp right primer | 5'CTAGTTCGAATCCTAGTACCTGTAGAGGTT 3' (SEQ ID NO:10) |

[1]Underlined bases form protruding ends for labeling with Klenow fragment after annealing with the complementary strand or PCR product.

EXAMPLE 2

A human hepatoblastoma cell line, Hep-G-2, obtainable from the ATCC under accession number HB 8065, contains a single base change at codon 61, CAA to CTA. Hsu et al.

(1990) Proc. Natl. Am. Assoc. Canc. Res., 31, 806. N-ras-containing nucleic acid fragments from normal cells and from Hep-G-2 cells were amplified by PCR using the appropriately configured primer oligonucleotides (SEQ ID NO:5 and SEQ ID NO:6), were hybridized with a complementary 107 base pair probe and then exposed to the A/G mismatch enzyme.

The 107 bp DNA (SEQ ID NO:3) probe comprises codons 48–81 of the N-ras gene with four extra nucleotides, TTGG, at the 5' end of the coding strand to serve as a template for labelling, except that the sequence for codon 61 is CGA. The probe generates a T/G and an A/G mismatch with the normal DNA and tumor DNA, respectively. The DNA's after cleavage with the A/G mismatch enzyme were denatured and separated on a sequencing gel using known methods. Maxam & Gilbert (1980) Meth. Enz., 65, 499–560.

Lanes containing tumor DNA presented a 44 base pair nucleotide cleavage product which was not found in normal DNA samples. When a shorter labelled probe of 50 base pairs (SEQ ID NO:4) was used and primers 3 and 4 (SEQ ID NO:7 and SEQ ID NO:8) were used to amplify the target sequence, the same results were found, that is, a nucleotide digestion product of the A/G mismatch enzyme, in that case, 26 base pairs, was found in the samples of tumor DNA but not in normal DNA.

EXAMPLE 3

To determine the sensitivity of the mismatch enzyme cleavage method, the N-ras-containing fragment of the Hep-G-2 liver cells and the 107 bp probe (SEQ ID NO:3) as noted in Table 2 described above were hybridized and the tumor DNA/probe hybrid was diluted with increasing amounts of hybrids comprising normal DNA and probe. The resulting mixtures then were cleaved with the E. coli A/G endonuclease as described above. A specific 44 base pair cleavage product remained detectable at the 1/50 dilution. Because the N-ras locus is heterozygous in the liver tumor cell from which the genomic DNA was obtained, the assay is sensitive up to 1 percent, that is tumor cells are present in only one percent of the normal cell background.

The disclosure in all references recited herein is herein incorporated by reference.

It will be evident to one of ordinary skill in the art that the invention described herein can be modified and adapted without departing from the spirit and scope thereof. The artisan will further acknowledge that the Examples recited herein are demonstrative only and are not meant to be limiting.

What is claimed is:

1. A method for identifying a nucleotide base pair at a point mutation site in a target double-stranded DNA molecule for which the corresponding wild-type DNA sequence has been determined, using a endonuclease that recognizes a base pair mismatch consisting of a first base and a second base, comprising:

(A) denaturing said target double-stranded DNA molecule comprising said point mutation site into a first single-stranded target DNA molecule and a second single-stranded target DNA molecule, wherein said first single-stranded target DNA molecule comprises a first DNA sequence and said second single-stranded target DNA molecule comprises a second DNA sequence complementary to said first DNA sequence;

(B) preparing a first, a second, a third and a fourth DNA probe, each comprising said mutation site, wherein said first and said second probes comprise said first DNA sequence, and said third and said fourth probes comprise said second DNA sequence, and wherein said first and said third probes contain at the mutation site said first base recognized by said mismatch endonuclease, and said second and said fourth probes contain at the mutation site said second base recognized by said mismatch endonuclease;

(C) hybridizing said first, second, third and fourth DNA probes with the resulting single-stranded target DNA molecules of step (A) to form DNA probe-target DNA hybrid molecules comprising said mutation site in individual reaction vessels in the following manner:

(1) said first DNA probe labelled with a detectable marker is hybridized to said second single-stranded target DNA molecule;

(2) said second DNA probe is hybridized to said second single-stranded target DNA molecule labelled with a detectable marker;

(3) said third DNA probe labelled with a detectable marker is hybridized to said first single-stranded target DNA molecule; and (4) said fourth DNA probe is hybridized to said first single-stranded target DNA molecule labelled with a detectable marker;

(D) exposing the resulting hybrid molecules of step (C) to said endonuclease, wherein said endonucleaee recognizes a mismatch base pair selected from the group consisting of A/G, A/C, T/G and T/C, and (1) binds to said mismatched base pair in said hybrid molecules to form an enzyme-DNA complex which is labelled, or (2) cleaves a errand containing said mismatched base to produce a cleaved DNA fragment which is labelled; and (E) assaying for the presence of said enzyme-DNA complex which is labelled or said cleaved DNA fragment which is labelled, (1) wherein when said endonuclease recognizes A/G or A/C, and forms a labelled enzyme-DNA complex or produces labelled cleaved DNA fragments when exposed to the hybrid molecule obtained in step (C) (4), said nucleotide base pair at said point mutation site is A/T, (2) wherein when said endonuclease recognizes T/G or T/C, and forms a labelled enzyme-DNA complex or produces labelled cleaved DNA fragments when exposed to the hybrid molecule obtained in step (C) (2), said nucleotide base pair at said point mutation site is A/T, (3) wherein when said endonuclease recognizes A/G or A/C, and forms a labelled enzyme-DNA complex or produces labelled cleaved DNA fragments when exposed to the hybrid molecule obtained in step (C) (2), said nucleotide base pair at said point mutation site is T/A, (4) wherein when said endonuclease recognizes T/G or T/C, and forms a labelled enzyme-DNA complex or produces labelled cleaved DNA fragments when exposed to the hybrid molecule obtained in step (C) (4), said nucleotide base pair at said point mutation site is T/A, (5) wherein when said endonucleaee recognizes A/G or T/G, and forms a labelled enzyme-DNA complex or produces labelled cleaved DNA fragments when exposed to the hybrid molecule obtained in step (C) (3), said nucleotide base pair at said point mutation site is G/C, (6) wherein when said endonuclease recognizes A/C or T/C, and forms a labelled enzyme-DNA complex or produces labelled cleaved DNA fragments when exposed to the hybrid molecule obtained in step (C) (1), said nucleotide base pair at said point mutation site te G/C, (7) wherein when said endonuclease recognizes A/G or T/G, and forms a labelled enzyme-DNA complex or produces labelled cleaved DNA fragments when exposed to the hybrid molecule obtained in step (C) (1), said nucleotide base pair at said point mutation site is C/G, and (8) wherein when said endonuclease recognizes A/C or T/C, and forms a labelled enzyme-DNA complex or produces labelled cleaved DNA fragments when exposed to the hybrid molecule obtained in step (C) (3), said nucleotide base pair at said point mutation site is C/G.

2. The method of claim 1 wherein said enzyme specifically binds to or cleaves at the adenine-guanine base pair.

3. The method of claim 1 where said enzyme specifically binds to or cleaves at the thymidine-guanine base pair.

4. The method of claim 1, wherein said detectable marker is a radioisotope.

5. The method of claim 1, wherein said detectable marker is an enzyme.

6. The method of claim 1, wherein said detectable marker is a dye.

7. The method of claim 1, wherein said enzyme produces cleaved fragments and each cleaved fragment is labelled with a different detectable marker.

8. The method of claim 1, wherein said target DNA molecule is obtained from a patient suspected of having a genetic disease.

9. The method of claim 8, wherein said target DNA molecule is obtained from blood cells, amniocytes or a biopsy specimen.

10. The method of claim 1, wherein said target DNA molecule is obtained from suspected cancer cells.

11. The method of claim 10, wherein said suspected cancer cells are obtained from blood, amniotic fluid or a biopsy specimen.

\* \* \* \* \*